United States Patent
Rennó

(10) Patent No.: US 9,297,755 B2
(45) Date of Patent: *Mar. 29, 2016

(54) ICE AND SUPERCOOLED WATER DETECTION SYSTEM

(71) Applicant: THE REGENTS OF THE UNIVERSITY OF MICHIGAN, Ann Arbor, MI (US)

(72) Inventor: Nilton O. Rennó, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/277,082

(22) Filed: May 14, 2014

(65) Prior Publication Data

US 2015/0120092 A1    Apr. 30, 2015

Related U.S. Application Data

(60) Provisional application No. 61/895,040, filed on Oct. 24, 2013.

(51) Int. Cl.
  *G01N 21/55*  (2014.01)
  *B60T 7/12*   (2006.01)
  (Continued)

(52) U.S. Cl.
  CPC . *G01N 21/55* (2013.01); *B60T 7/12* (2013.01); *B64D 15/20* (2013.01); *B64D 15/22* (2013.01); *G01N 21/27* (2013.01); *G01N 21/314* (2013.01);
  (Continued)

(58) Field of Classification Search
  CPC ............. B64D 15/20; B64D 15/22; G01N 2033/1873; G01N 21/314
  See application file for complete search history.

(56) References Cited

U.S. PATENT DOCUMENTS 4,274,091 A * 6/1981 Decker .................. 340/583
4,441,363 A   4/1984 Hill et al.
(Continued)

FOREIGN PATENT DOCUMENTS

JP  2006046936 A  2/2006
JP  4492883 B2    6/2010

OTHER PUBLICATIONS

International Search Report and Written Opinion, International Application No. PCT/US2014/047415, dated Nov. 20, 2014, 12 pages.

(Continued)

*Primary Examiner* — Mussa A Shaawat
(74) *Attorney, Agent, or Firm* — Harness, Dickey & Pierce, PLC

(57) ABSTRACT

A system for detecting ice or supercooled large droplets within an area of interest having a detection system measuring radiance or reflectance of the area of interest when exposed to shortwave infrared radiation having a wavelength in the range of about 2.05 μm to about 2.30 μm. The detection system measures the radiance or reflectance in a first band having a wavelength in the range of about 2.05 μm to about 2.15 μm and outputting a first band signal, and further measures the radiance or reflectance in a second band having a wavelength in the range of about 2.15 μm to about 2.30 μm and outputting a second band signal. A processing unit determines a ratio of the first band signal and the second band signal and compares the ratio to a predetermined critical ratio and outputs a determination signal indicating presence of ice or supercooled water droplets.

20 Claims, 8 Drawing Sheets

(51) Int. Cl.
  *B64D 15/22* (2006.01)
  *G01N 21/27* (2006.01)
  *G01N 33/18* (2006.01)
  *B64D 15/20* (2006.01)
  *G01N 21/31* (2006.01)
  *G01N 21/35* (2014.01)
  *G01N 21/3554* (2014.01)
  *G01N 21/3563* (2014.01)

(52) U.S. Cl.
  CPC ............ *G01N 21/35* (2013.01); *G01N 21/3554* (2013.01); *G01N 21/3563* (2013.01); *G01N 33/18* (2013.01); *G01N 2033/1873* (2013.01); *G01N 2201/061* (2013.01); *G01N 2201/12* (2013.01)

(56) References Cited

U.S. PATENT DOCUMENTS

| | | | |
|---|---|---|---|
| 4,804,849 A | 2/1989 | Booth et al. | |
| 4,809,197 A * | 2/1989 | Tashiro et al. | 702/35 |
| 4,819,480 A | 4/1989 | Sabin | |
| 4,965,573 A | 10/1990 | Gallagher et al. | |
| 4,984,163 A * | 1/1991 | Kuwana et al. | 701/80 |
| 5,028,929 A | 7/1991 | Sand et al. | |
| 5,218,206 A * | 6/1993 | Schmitt | B60R 16/0237 250/339.1 |
| 5,497,100 A | 3/1996 | Reiser et al. | |
| 5,521,594 A * | 5/1996 | Fukushima | 340/901 |
| 5,596,320 A | 1/1997 | Barnes | |
| 5,796,344 A * | 8/1998 | Mann et al. | 340/583 |
| 5,818,339 A * | 10/1998 | Giles et al. | 340/583 |
| 5,905,570 A | 5/1999 | White et al. | |
| 6,091,335 A | 7/2000 | Breda et al. | |
| 6,161,075 A | 12/2000 | Cohen | |
| 6,166,645 A * | 12/2000 | Blaney | 340/583 |
| 6,166,657 A | 12/2000 | Mann | |
| 6,269,320 B1 | 7/2001 | Otto | |
| 6,384,611 B1 | 5/2002 | Wallace et al. | |
| 6,430,996 B1 * | 8/2002 | Anderson | B64D 15/20 73/170.26 |
| 6,459,083 B1 | 10/2002 | Finkele et al. | |
| 6,819,265 B2 | 11/2004 | Jamieson et al. | |
| 6,921,898 B1 | 7/2005 | Chen | |
| 6,977,597 B2 | 12/2005 | Doherty | |
| 7,100,427 B2 | 9/2006 | Kahn et al. | |
| 7,104,502 B2 | 9/2006 | Otto et al. | |
| 7,119,891 B2 | 10/2006 | White et al. | |
| 7,224,453 B2 | 5/2007 | Elman | |
| 7,265,846 B2 | 9/2007 | Forsyth | |
| 7,301,478 B1 | 11/2007 | Chinn et al. | |
| 7,370,525 B1 | 5/2008 | Zhao et al. | |
| 7,424,399 B2 | 9/2008 | Kahn et al. | |
| 7,839,301 B2 | 11/2010 | Doherty et al. | |
| 7,986,408 B2 | 7/2011 | Ray et al. | |
| 8,000,847 B2 | 8/2011 | Shue | |
| 8,044,823 B2 | 10/2011 | Doherty et al. | |
| 8,325,338 B1 | 12/2012 | Pope et al. | |
| 8,350,910 B2 | 1/2013 | Capello et al. | |
| 8,796,627 B2 | 8/2014 | Rockwell et al. | |
| 9,013,332 B2 | 4/2015 | Meis | |
| 2002/0162962 A1 * | 11/2002 | Rudolph | 250/339.1 |
| 2003/0150992 A1 | 8/2003 | Chavez et al. | |
| 2003/0169186 A1 * | 9/2003 | Vopat | G08B 19/02 340/962 |
| 2004/0036630 A1 * | 2/2004 | Jamieson | B64D 15/20 340/962 |
| 2004/0231410 A1 | 11/2004 | Bernard et al. | |
| 2005/0002435 A1 | 1/2005 | Hashimoto et al. | |
| 2005/0100336 A1 * | 5/2005 | Mendenhall et al. | 398/27 |
| 2005/0105103 A1 | 5/2005 | Schietinger et al. | |
| 2005/0151965 A1 | 7/2005 | Bissett et al. | |
| 2005/0167593 A1 * | 8/2005 | Forsyth | G01N 21/314 250/339.11 |
| 2005/0218268 A1 | 10/2005 | Otto et al. | |
| 2005/0230553 A1 | 10/2005 | Otto et al. | |
| 2006/0050270 A1 | 3/2006 | Elman | |
| 2006/0261975 A1 * | 11/2006 | Fridthjof | 340/905 |
| 2007/0074415 A1 * | 4/2007 | Gagnon | B64D 15/20 33/630 |
| 2008/0110254 A1 | 5/2008 | Zhao et al. | |
| 2008/0129541 A1 * | 6/2008 | Lu et al. | 340/905 |
| 2008/0218385 A1 | 9/2008 | Cook et al. | |
| 2009/0222238 A1 * | 9/2009 | Gagnon | G01B 11/0625 702/172 |
| 2010/0085175 A1 | 4/2010 | Fridthjof | |
| 2010/0110431 A1 * | 5/2010 | Ray | B64D 15/20 356/342 |
| 2011/0135197 A1 | 6/2011 | Paris et al. | |
| 2012/0085868 A1 | 4/2012 | Barnes | |
| 2012/0140233 A1 | 6/2012 | Rockwell et al. | |
| 2012/0193477 A1 * | 8/2012 | Thore | B64D 15/20 244/134 F |
| 2012/0266669 A1 | 10/2012 | Sage | |
| 2012/0274938 A1 * | 11/2012 | Ray | 356/342 |
| 2012/0327410 A1 | 12/2012 | Maston | |
| 2014/0112537 A1 | 4/2014 | Frank et al. | |
| 2014/0372069 A1 | 12/2014 | Nuzzio | |

OTHER PUBLICATIONS

International Search Report and Written Opinion, International Application No. PCT/US2014/038003, dated Aug. 14, 2014, 13 pages.

Kou, L., Labrie, D., and Chylek, P., "Refractive indices of water and ice in the 0.65- to 2.5μm spectral range", (Jul. 1993), Appl. Opt., 32(19), 3531-3540.

Rennó, N. O., et al., "CHASER: An Innovative Satellite Mission Concept to Measure the Effects of Aerosols on Clouds and Climate", (May 2013), Bull. Amer. Meteor. Soc., 94, 685-694.

Vanderlei Martins, J., et al., "Remote sensing the vertical profile of cloud droplet effective radius, thermodynamic phase, and temperature", (Mar. 2007), Atmos. Chem. Phys. Discuss., 7, 4481-4519.

\* cited by examiner

ICE AND SUPERCOOLED WATER DETECTION SYSTEM

CROSS-REFERENCE TO RELATED APPLICATIONS

This application claims the benefit of U.S. Provisional Application No. 61/895,040, filed on Oct. 24, 2013. The entire disclosure of the above application is incorporated herein by reference.

FIELD

The present disclosure relates to an optical system capable of detecting ice on a wide variety of surfaces, such as bridges, roads, sidewalks, railways, runaways, for use with ground-based vehicles and further capable of detecting supercooled water droplets that freeze when impacting the surfaces of airborne vehicles, such as aircrafts, Unmanned Air Vehicles (UAVs) and other objects of interest.

BACKGROUND AND SUMMARY

This section provides background information related to the present disclosure that is not necessarily prior art. This section further provides a general summary of the disclosure, and is not a comprehensive disclosure of its full scope or all of its features.

The detection of ice and associated icing conditions is an important factor in maximizing safety associated with various modes of transportation. It is well known that ice accumulation on surfaces can lead to an increased occurrence of vehicle accidents, personal injuries resulting from falls, and disruptions in transportation and other human activities.

In connection with vehicle travel, roadway ice can often occur in in ways that are difficult for a prudent driver to detect. Such ice—often referred to as 'slippery ice' or 'black ice'—is usually smooth and translucent. Similarly, in connection with aircraft travel, airborne icing conditions can often occur in ways that are difficult for a pilot to discern. Airborne icing can occur in nearly all regions of the globe throughout the year, making detection and avoidance important for flight safety.

Unfortunately, few systems exist that are capable of reliably detecting the presence of ice or icing conditions and providing an associated alert. In terms of ground-based vehicles, such as cars, trucks, trains, automated people movers, rails, monorails, metros, buses, motorcycles, bicycles, and similar vehicles, there is a surprising lack of suitable systems for detecting and warning users of the presence of ice on surfaces, such as roadways, bridges, railways, sidewalks, or even taxiways (such as in connection with ground operations of aircraft). In fact, ice detection in most vehicles merely includes a simple notification once the air temperature is at or near the freezing point of water. However, unfortunately, this is not typically indicative of the presence of surface ice that may affect safety and/or drivability of a vehicle. This invariably leads to a high number of accidents and fatalities due to drivers and operators being unaware of deteriorating conditions or false alerts that are ultimately disregarded by a driver or operator. In terms of airborne-based vehicles, such as aircrafts, helicopters, UAVs, and similar vehicles, additional systems are available, but each suffers from a number of disadvantages.

Prior art approaches for detecting slippery ice on surfaces, such as roads, use an imager capable of measuring the polarization of the light reflected by slippery ice. However, it should be understood that although light is polarized when reflected by dielectric materials, such as ice, ice is not the only dielectric material that polarizes light. In fact, reflections by wet and/or oily surfaces also cause polarization, which would lead to false reporting of ice. Therefore, polarization is not capable of distinguishing among the possible types of dielectric materials reflecting light. Consequently, it cannot be used to detect the presence of ice unambiguously. For example, U.S. Pat. No. 2008/0129541A1 refers to a slippery ice warning system capable of monitoring the road ahead of a vehicle. One or two cameras are used to image the same scene at two orthogonal polarizations. When a single camera is used, a polarization beam splitter is used to separate the reflected light into two orthogonal polarizations. The possible (but ambiguous) determination of the existence of slippery ice ahead of the vehicle is detected by measuring the polarization of the reflected light. However, again, this system is unable to discern whether the detected polarization is due to ice or some other reflective material.

Additional ice detection systems are based on in-situ measurements and are only applied to airborne applications. For example, U.S. Pat. No. 7,104,502 is for a system capable of detecting the accumulation of ice by measuring changes in the vibration frequency of a strut exposed to the airflow on an aircraft. The strut contains at least one feature that allows ice to accrete on it at higher rate than in other parts of the aircraft. Similarly, U.S. Pat. No. 7,370,525 refers to a dual channel inflight system that detects ice accretion on aircraft surfaces. The system illuminates the surface of the aircraft with linearly polarized light. Light conductors with polarization sensitivity aligned to the transmitted light, and with polarization sensitivity orthogonal to it, acquire the backscattered light. The ratio of the intensities of the light in the two conductors is used to detect the presence of ice.

Moreover, U.S. Pat. No. 6,269,320 describes an in-situ Supercooled Large Droplet (SLD) detector. This system takes advantage of boundary layer flow patterns to detect SLD. It is capable of distinguishing between the presence of water droplets that cause regular cloud icing and SLD icing. However, this system detects ice after it accumulates on aircrafts surfaces and thus does not give warnings before a hazards situation occurs. In particular, it does not detect supercooled liquid water droplets in the airspace around aircrafts.

In some cases, prior art approaches for distinguishing between liquid water and ice particles in the airspace ahead of aircrafts measure the depolarization of the backscattered light emitted by a polarized laser beam. U.S. Pat. No. 6,819,265 refers to an ice warning system capable of monitoring the airspace ahead of the aircraft. The system contains a laser source, optical elements to direct the laser beam into the airspace ahead of the aircraft and to receive the laser light backscattered by the targets, optical elements to separate the received laser light into various wavelengths and to direct them into light detectors, and a processor to conduct the calculations necessary to generate warnings. U.S. Pat. No. 7,986,408 refers to an airborne active system that employs both linear and circular polarizations to detect water droplets and ice particles in the airspace ahead of an aircraft.

According to the principles of the present teachings, an ice and supercooled water detection system is provided that overcomes the disadvantages of the prior art and is particularly useful in ground-based and airborne-based applications. In most embodiments of the present teachings, the system detects ice unambiguously by making multi-spectral measurements of radiance. In some embodiments, the system can be passive but a light source can be included, detectors and/or a shortwave infrared (SWIR) camera with two filters, a data processor unit, and interfaces with displays, safety systems, and/or flight systems provide an indication of icing and a response to it.

Still further, in some conventional airborne applications, the detection of icing conditions in the airspace ahead of an aircraft requires systems capable of actually distinguishing between supercooled liquid water droplets and ice particles. Accordingly, in some embodiments of the present teachings, the system is capable of detecting liquid water droplets and ice particles in an area of interest of the airspace, and of estimating the size of potentially hazardous supercooled liquid water droplets. This embodiment increases aviation safety by adding the capability of detecting icing conditions and Supercooled Large Droplets (SLD) to flight displays such as Enhanced Vision Systems (EVS).

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations. They are not intended to limit the scope of the present disclosure.

FIG. 1 is a graph showing the imaginary part of the complex index of refraction of liquid water and ice, indicating that reflectance (or simple radiance as justified below) measurements at shortwave infrared (SWIR) spectral bands between about 2.00 and 2.15 µm and between about 2.15 and 2.30 µm can be used to distinguish liquid water droplets from ice particles.

Corresponding reference numerals indicate corresponding parts throughout the several views of the drawings.

DETAILED DESCRIPTION

Figure 1:
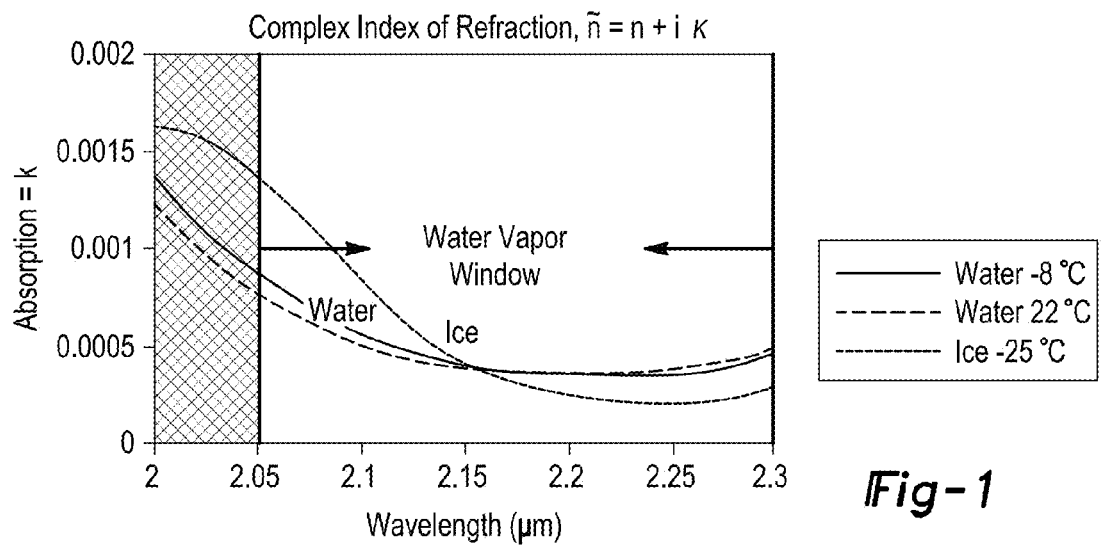

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present teachings, an ice and supercooled water detection system 10 is provided having a light source 12, at least one detector 14, a data processing unit 16, and an output system 18. These components will be described in greater detail herein. However, it should be understood that the present teachings provide utility in a wide variety of applications, including ground-based and airborne-based applications. More particularly, and without limitation, the present teachings are well-suited for use in ground-based applications, including detecting ice on bridges, roadways, railways, ramps, sidewalks, building entrances, building decks, garages and parking areas, runways and taxiways, marinas, boat decks, platforms, and any other surface subject to icing. It should be understood that such ground-based applications can further monitoring at fixed locations or regions, such as on bridges, buildings, garages, roadways, or similar locations. Moreover, the present teachings can be incorporated into a number of ground-based vehicles, such as, but not limited to, cars, trucks, trains, automated people movers, rails, monorails, metros, buses, motorcycles, bicycles, aircraft (taxiing), and similar vehicles, and ground-based infrastructure locations, such as on poles, buildings, elevated locations, road barriers, and the like.

It should further be understood that the present teachings can be incorporated into a number of airborne-based vehicles, such as, but not limited to, aircraft including engines, turbines, propellers, blades, air intakes, control surfaces, wings, stabilizers, and other components of aircraft; helicopters; UAVs; blimps; balloons (e.g. weather balloons); and other objects of interest.

In all applications, the particular mounting location is not necessarily crucial, so long as proper illumination and detection performance is maintained. Therefore, the present teachings should not be regarded as being limited to any one particular mounting location on ground-based vehicles, ground-based infrastructure, or airborne-based vehicles.

Fundamental Principles

At the outset, it is important to understand various fundamental principles that are employed as part of the present teachings. To this end, it should be understood that liquid water and ice exhibit fundamental characteristics when exposed to light, in particular at shortwave infrared (SWIR) spectral bands. For purposes of the present discussion, these SWIR spectral bands are typically in the range of about 2.05 to 2.30 μm (spectrum range of interest). Generally, 2.05 μm has been determined to be a lower limit due to the fact that the atmosphere tends to absorb a greater portion of the light below 2.05 μm, thereby negatively affecting detection efficiency. However, at wavelengths between about 2.05 and 2.30 μm atmospheric absorption is negligible and the absorption properties of liquid water and ice exhibit predictable characteristics (Kuo et al., 1993; Martins at al., 2007) that allows the detection of ice and liquid water as illustrated in FIG. 1. As discussed below, shortwave infrared (SWIR) spectral bands between about 2.05 and about 2.15 μm and between about 2.15 and about 2.30 μm can be used to distinguish liquid water droplets from ice particles unambiguously. This range (2.05-2.30 μm) is generally referred to as a 'water vapor window.'

Upon careful review of FIG. 1, one will note that a transition or crossover occurs at about 2.15 μm where the absorption characteristics of liquid water invert relative to the absorption characteristics of ice. In this way, comparison of the absorption of liquid water and ice in this water vapor window or spectrum range of interest (about 2.05 μm to about 2.30 μm), specifically using measurements of reflectance or radiance obtained from opposing sides of this transition or crossover point (about 2.15 μm), permits one to detect/determine the presence of liquid water or ice unambiguously. Thus, by measuring the radiance/reflectance at wavelengths on opposing sides of this crossover point, one can determine the presence of liquid water or ice based on a ratio of the measured radiance/reflectance. Ideally, these regions on the opposing sides of the crossover point provide optimal spectral bands leading to unambiguous detection—namely a first optimal spectral band of about 2.05 to 2.15 μm (hereafter referred to as the 2.10 μm band) and another optimal spectral band of about 2.20 and 2.30 μm (hereafter referred to as the 2.25 μm band).

It should be understood that although the present teachings are directed to the measurement of radiance, measurements of reflectance can similarly be used. However, it should be noted that radiance measurements (instead of reflectance measurements) are simpler and typically sufficient for practical applications because typical targets of interest are illuminated with light sources containing relatively small or known power variations between 2.05 and 2.30 μm (e.g., clouds or surfaces illuminated by direct or indirect sunlight, or illuminated by a known light source). Therefore, the present teachings should not be regarded as being limited to only radiance measurements as reflectance measurements are also anticipated.

Figure 2A:
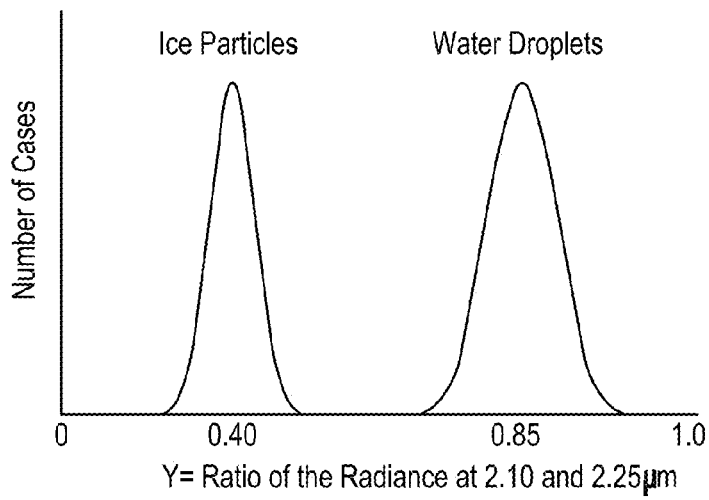
FIG. 2A is a probability distribution sketch illustrating that the radiance ratio ($\gamma$) can be used to distinguish water droplets from ice particles.
Figure 2B:
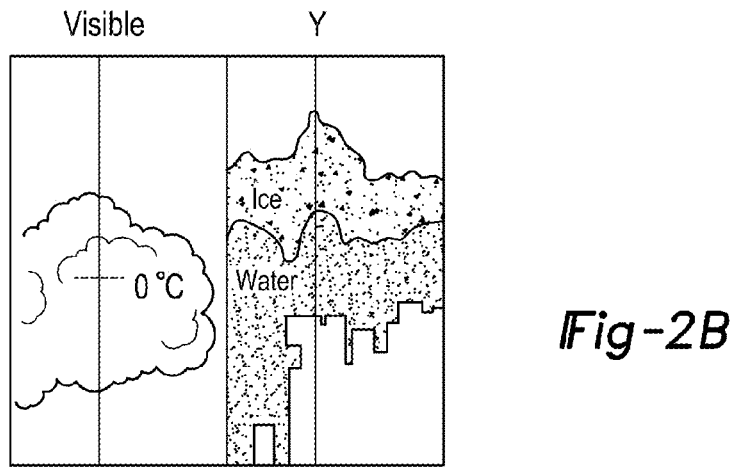
FIG. 2B shows radiance ratios derived from measurements of a convective cloud indicating that regions of liquid water can be distinguished from regions of ice particles, based on calculations of $\gamma$, the ratio of the spectral reflectances at 2.10 µm and 2.30 µm.

With reference to FIG. 2A, a probability distribution sketch is provided illustrating that a radiance ratio ($\gamma$) can be used to distinguish water droplets from ice particles. In some embodiments, a radiance ratio of about 0.40 can indicate the presence of ice particles and a radiance ratio of about 0.85 can indicate the presence of water droplets. As will be discussed herein, the exact ratio may be irrelevant so long as the radiance ratio is greater than or less than a predetermined critical ratio. Ice has a relatively low radiance ratio that allows it to be detected when deposited on materials such as soils, concrete, and asphalt for example. With reference to FIG. 2B, radiance ratios are illustrated in connection with measurements of a convective cloud indicating regions of liquid water and ice particles, based on calculations of $\gamma$, the ratio of the spectral reflectances at 2.10 μm and 2.30 μm.

Figure 3A:
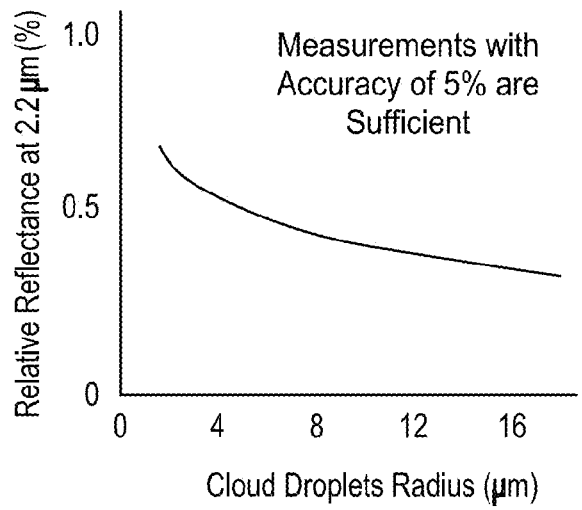
FIG. 3A is a 'Twomey diagram' indicating that relative reflectance at about 2.2 µm (R) can be used to estimate cloud droplet radius.

Turning now to FIG. 3A, a 'Twomey diagram' is provided indicating that reflectance values (or radiance values) can be used to determine cloud droplets size. This can be achieved because, at fixed cloud optical thickness ($\tau$), the reflectance at around 2.2 μm (R) decreases with cloud droplet size at the rate of approximately $(k\,r_e)^{1/2}$, where k is the absorption coefficient (the imaginary part of the index of refraction) of water and $r_e$ is the cloud droplet (effective) radius (Twomey and Seton, 1980). The dependence of cloud reflectance on droplet size is caused by the fact that absorption by liquid water increases relative to scattering with increases in droplet size.

For thick clouds, the effect of changes in cloud optical thickness is negligible. Therefore, the relationship between reflectance and cloud droplet radius provided by the 'Twomey diagram' is an excellent approximation for thick clouds (clouds of large optical thickness). Measurements at other absorbing wavelengths can also be used to determine cloud droplet (effective) radius, for example at around 3.7 µm. The determination of cloud droplet size can be refined using measurements of radiance at a non-absorbing wavelength as described herein.

Figure 3B:
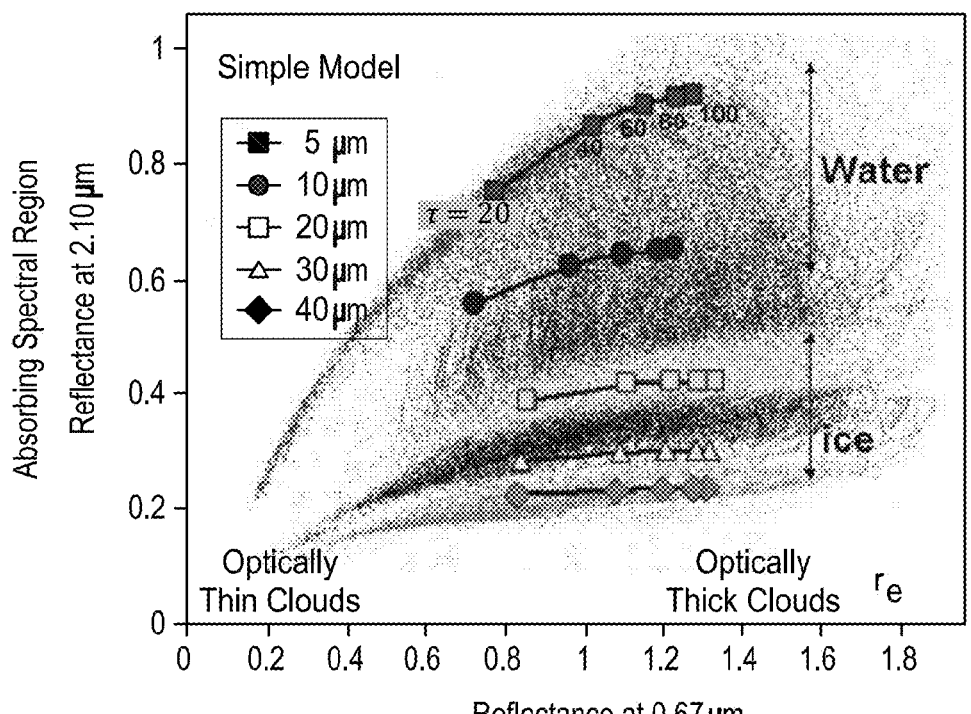
FIG. 3B is a 'Nakajima-King diagram' indicating that reflectance values (or radiance values) in absorbing and non-absorbing spectral bands can be used to determine cloud droplets' size.

FIG. 3B illustrates a 'Nakajima-King diagram' indicating that reflectance values (or radiance values) in absorbing and non-absorbing spectral bands can be used to determine cloud droplets' size (Martins et al., 2007), even when the optical thicknesses are variable or small such as in light drizzle or rain. The measurements at non-absorbing wavelengths also mitigate the effects of variations in illumination such as shadowing. Rain usually occurs when $r_e$>10-15 µm, but Supercooled Large Droplets (SLD) can have radius of up to 2.5 mm. Aircrafts certified for flights into icing conditions can handle droplets of radius of up to about 25 µm. Unfortunately, droplets this large are not uncommon in convective clouds.

During operation, water droplets and ice particles can be detected in/on aircraft surfaces and/or airspace (immediately adjacent an aircraft when in clouds and ahead of an aircraft when the aircraft is flying outside clouds). To this end, as will be discussed herein, the ice and supercooled water detection system 10 can comprise a forward looking camera or detector 14 for making measurements of the radiance in the aforementioned two spectral bands. In some embodiments, an in-situ sensor for making measurements of the outside temperature can further be used. Algorithms are provided for detecting supercooled liquid water droplets and estimating the size of the droplets as described in FIGS. 4, 5A and 5B.

During night operations, such as airborne-based applications, clouds in the airspace immediately ahead of an aircraft can be illuminated with light sources containing the desired spectrum. In some embodiments, light source 12 can be used to illuminate the airspace around the aircraft while the radiance can be measured via detector 14. In more complex embodiments, clouds in the airspace miles ahead of the aircraft can be illuminated with laser beams containing the desired spectrum. However, such complexity may not be required in most applications as simpler embodiments of the present teachings can be used to detect icing hazards before ice accumulation occurs and therefore the aircraft can be maneuvered safely away from areas of icing.

System Description

In some embodiments, as referenced herein, light source 12 can comprise any source that is capable of outputting light (or radiation energy) within a predetermined light spectrum band. As described herein, it is desired to perform detection at a light spectrum band, or a combination of light spectrum bands in the shortwave infrared (SWIR) spectral bands, including the range of about 2.05 µm to about 2.30 µm. More particularly, in some embodiments, light source 12 can output light at a single spectral band covering the range of interest from about 2.05 µm to about 2.30 µm. However, in some embodiments, light source 12 can output light covering two or more spectral bands, such as about 2.05 µm to about 2.15 µm and a second spectral band of about 2.15 µm to about 2.30 µm (or about 2.20 µm to about 2.30 µm).

Still further, in some embodiments, light source 12 can comprise any light source capable of outputting light in the shortwave infrared (SWIR) spectral bands, including lasers, halogen lights, infrared lights, light-emitting diodes, and the like. It should also be understood that alternative light sources can be used, such as naturally occurring light sources (e.g. sunlight, etc.). Therefore, it should be recognized that in some embodiments the present teachings do not require a supplied or otherwise powered light source, but may rely on sunlight or other naturally occurring or separately provided light sources.

In some embodiments, detector 14 can comprise any suitable detector or camera/imaging system capable of detecting and/or monitoring radiance and/or reflectance at spectral bands that allows the detection of liquid water and/or ice. It should be understood that in some embodiments, detector 14 can be based on Indium Gallium Arsenide (InGaAs) technology, or can include or employ photodetectors, photodiodes, pyroelectric detectors, thermopile detectors, photoconductors, and other sensors, detectors, or cameras. In some embodiments, detector 14 can comprise a single detector, camera, or other device for measuring radiance and/or reflectance. However, in some embodiments, detector 14 can comprise two or more detectors, cameras, or other devices that are each suitable for measuring radiance and/or reflectance for a specific spectrum range that is narrower than the total spectrum range of interest. In other words, a first detector can be used to detect radiance and/or reflectance in connection with spectrum in the about 2.05 µm to about 2.15 µm range while a second detector can be used to detect radiance and/or reflectance in connection with spectrum in the about 2.20 µm to about 2.30 µm range. This arrangement can permit monitoring and/or detection to occur simultaneously when used with a light source 12 that outputs the spectral range of interest. In some embodiments, detector 14 can comprise one or more cameras or detectors having a filter system 20 that employs a plurality of filters to limit the detection of received wavelengths to a predetermined spectral band. That is, a filter can be used to allow light in association with the about 2.05 µm to about 2.15 µm range to be detected while a second filter can be used to allow light in association with the about 2.20 µm to about 2.30 µm range to be detected. Irrespective of the method of measuring and/or monitoring the reflected/received light, detector 14 outputs a detector signal representative to the measured radiance/reflectance.

In some embodiments, data processing unit 16 can comprise any suitable processing unit capable of determining a ratio of radiance measured at the first spectral band and at the second spectral band in response to the detector signal. Data processing unit 16 can comprise a central processing unit (CPU), in some embodiments, or may further simply be implemented through hardware design. Data processing unit 16 can further implement the algorithms described herein and output an output signal.

Finally, the output signal can be received by output device 19 and, in some embodiments, further processed in connection with other vehicle systems, such as alert displays, traction control, ABS, deicing or anti-icing equipment, or other systems or warnings.

Figure 8A:
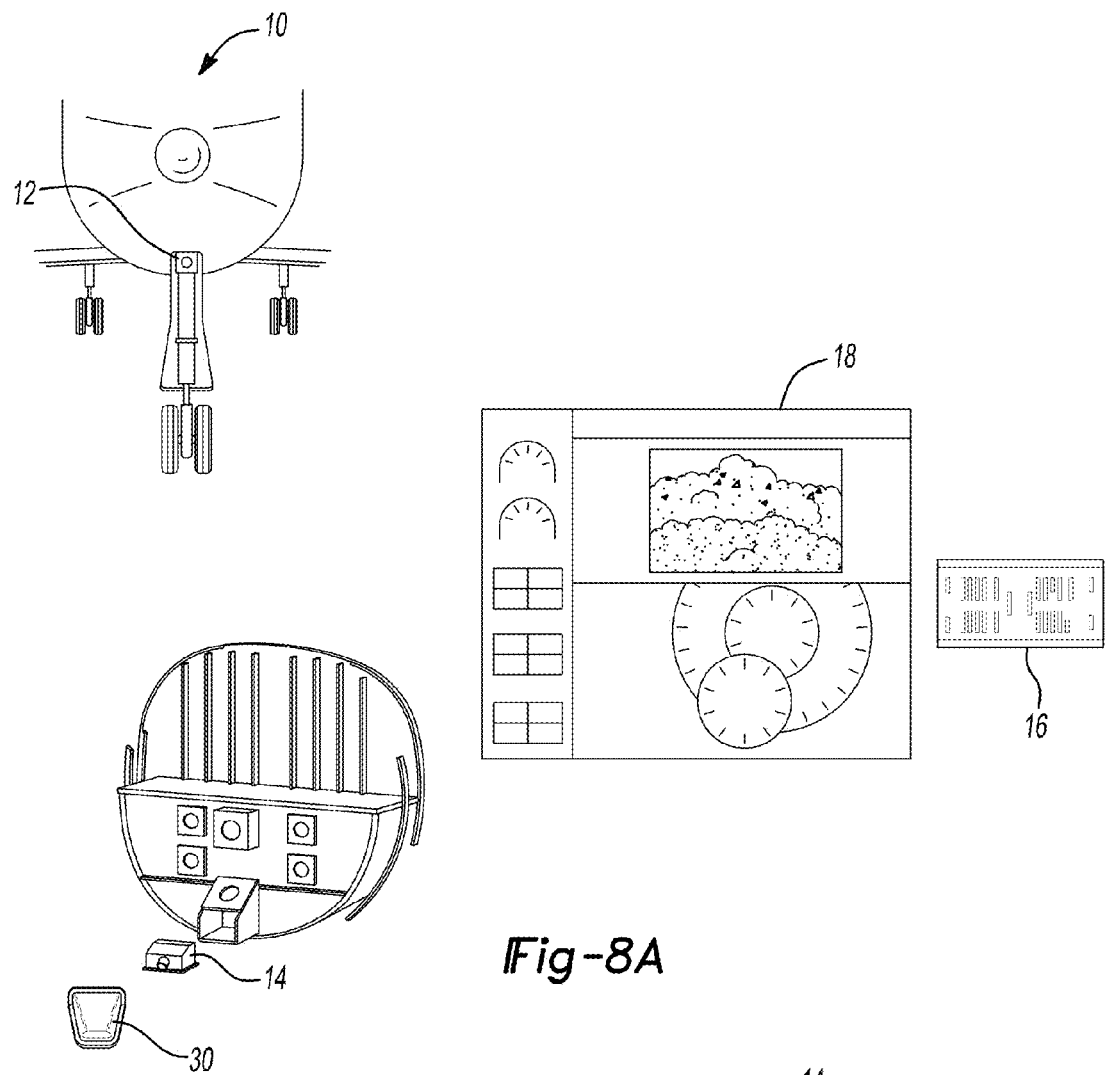
FIG. 8A illustrates ice and supercooled water detection system for use in connection with airborne-based applications.
Figure 8B:
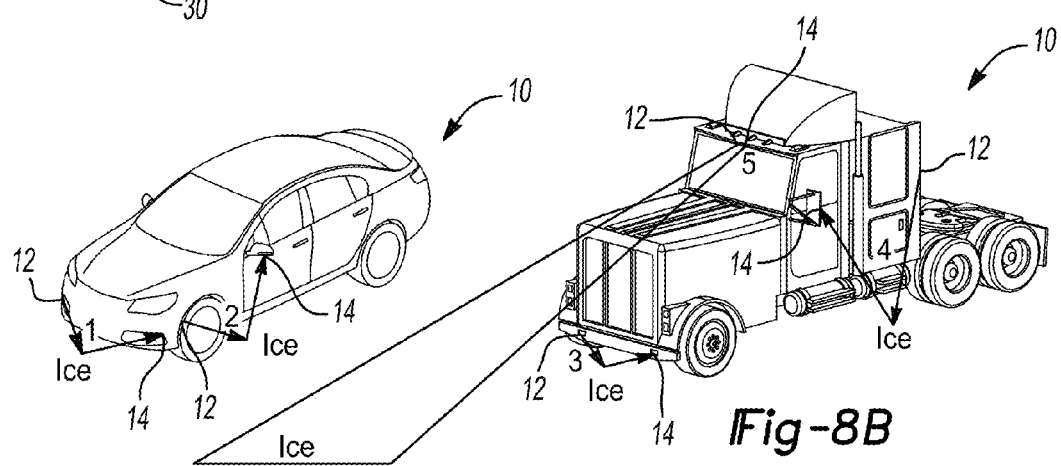
FIG. 8B illustrates ice and supercooled water detection system for use in connection with ground-based applications.

With particular reference to FIGS. 8A, 8B, ice and supercooled water detection system 10 is illustrated in accordance with some embodiments of the present teachings. Ice and supercooled water detection system 10 is illustrated for particular use in connection with the detection of supercooled liquid water and SLD by aircrafts, helicopters and UAVs. Ice and supercooled water detection system 10 can be implemented easily in flight systems such as EVS containing cameras covering the about 2.05-2.30 µm spectral band. In such embodiments, only filters in the 2.10 µm and 2.25 µm spectral bands and image processing software are necessary for the implementation of the system. These two filters can be implemented in a chessboard like grid or in stripes. This enables the reflectance at the two spectral bands of interest to be measured in nearby pixels, avoiding the need for moving parts or multiple cameras. Indeed, it allows the implementation of the ice/water detection algorithm while maintaining current EVS functions with only minor degradation in image resolution. In some embodiments, vertical filter strips can be used to achieve the necessary multi-spectral measurements along the flight path without affecting the rest of the image. Therefore, supercooled liquid water and SLDs can be detected easily by implementing the algorithms described in FIGS. 4, 5A and/or 5B to some existing EVS systems.

It should be understood that the detector 14 can be mounted anywhere on the vehicle, including the nose cone of an aircraft. Detector 14 can be mounted external or internal to the vehicle. However, it should be recognized that any protective coverings or windows 30 placed in front of detector 14 must permit transmission of the radiance spectrum of interest (e.g. must be transparent to shortwave infrared). Temperature sensors, thermostats, and/or heaters can be used with the coverings or windows to ensure proper transmission.

With particular reference to FIG. 8B, ice and supercooled water detection system 10 is illustrated for particular use in connection with ground-based vehicles. In some embodiments, light source 12 can be mounted under a front end of the vehicle and the corresponding detector 14 can be mounted in a complementary position to detect radiance/reflectance of the light source off the surface of interest. In this way, the front of the vehicle can be used to maximize the angle (measured from zenith) of incidence (and reflection) on the surface. This is done to maximize reflectance because it increases with the angle of incidence.

In some embodiments, light source 12 can be mounted along a wheel well edge or other side panel and detector 14 can be mounted in a side panel or side view mirror, while maximizing reflectance. Still further, in some embodiments, ice and supercooled water detection system 10 can be used to detect ice ahead of the vehicle (rather than beneath or the side of the vehicle). In this way, light source and detector 14 can be mounted at an elevated position and projected forward of the vehicle.

Specular reflection can be determined by imaging the area of interest ahead of the vehicle with an auxiliary camera. If the radiance of an area of the image is significantly higher (for example, a few standard deviations above) than the mean value, these "bright" image pixels are flagged as containing specular reflection, an indication of slippery ice. Other statistical criteria could also be used to determine specular reflection. If the criteria for specular reflection are met and ice is detected anywhere around the vehicle ($\gamma > \gamma_{crit}$) the image pixels containing specular reflection are flagged as containing slippery ice. This allows the areas ahead of the vehicle likely containing slippery ice to be mapped, displayed, and this information to be used by safety systems and/or the driver.

Figure 8C:
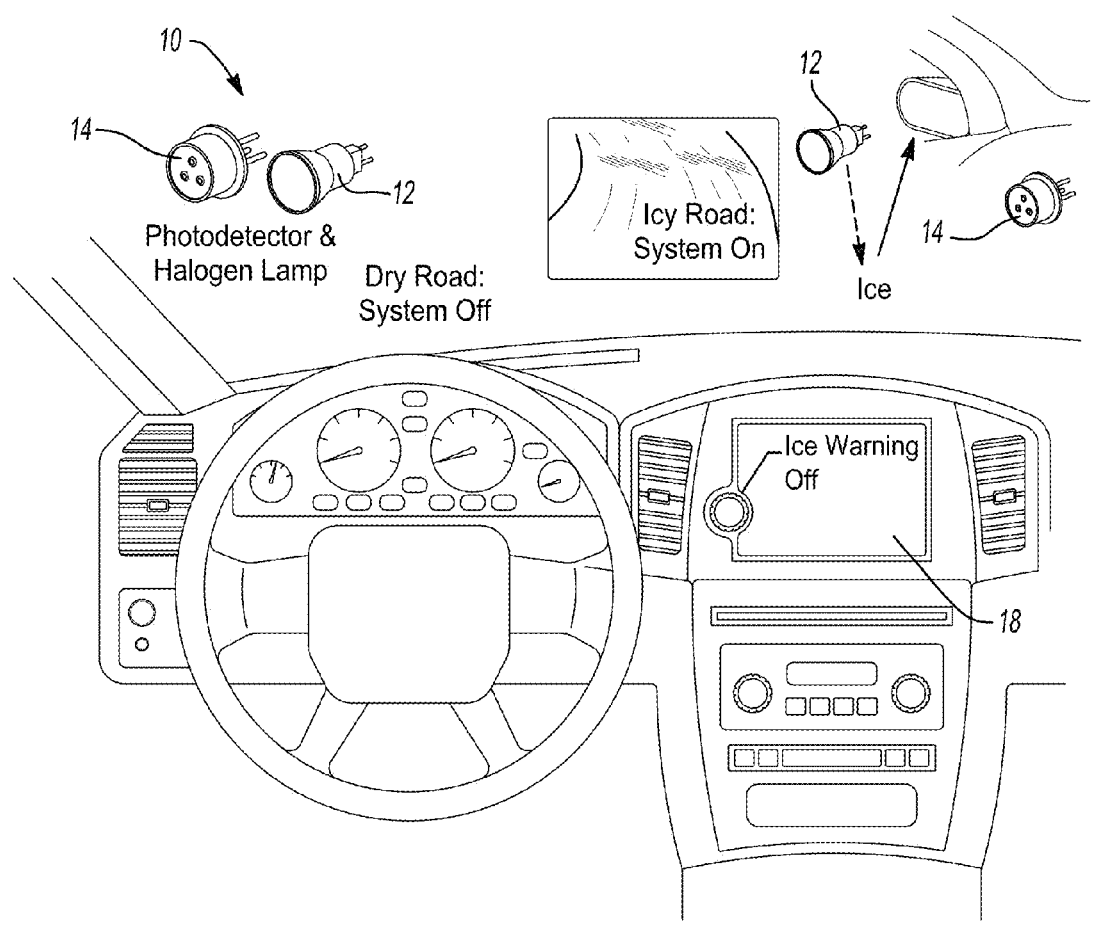
FIG. 8C illustrates a simplified ice and supercooled water detection system.

With particular reference to FIG. 8C, ice and supercooled water detection system 10 can comprise both light source 12 and detector 14 being mounted in the side mirror of a vehicle. The system is thus optimized for simplicity in the detection of both specular reflection and reflectance. As described herein, air or ground temperature measurements can be used to further mitigate false alarms.

Methods of Ground-Based Applications

Figure 6:
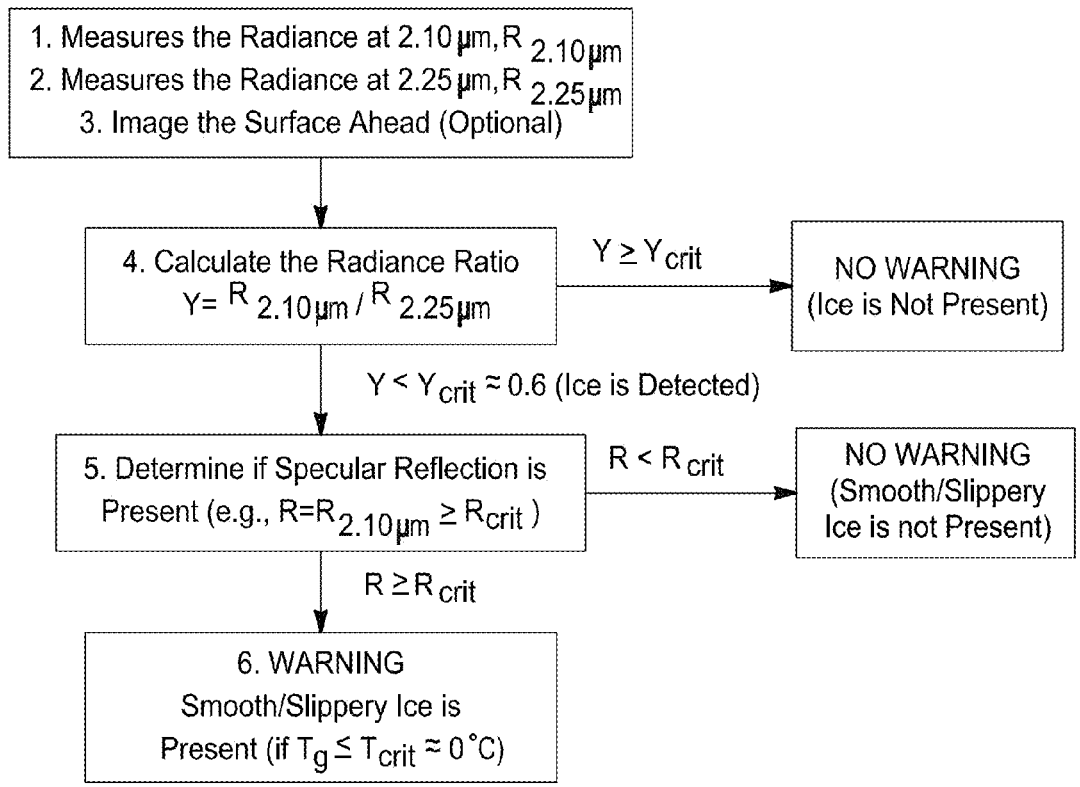
FIG. 6 is a description of an algorithm for determining the presence of ice on runaways, roads and other surfaces of interest.

In some embodiments, a method and/or algorithm is provided for detecting slippery ice in connection with ground-based applications. As illustrated in FIG. 6, the method can comprise the steps of:

1. A SWIR camera or detectors 14 with spectral filters between about 2.05 and 2.15 μm are used to measure the radiance of the area of interest at about 2.10 μm ($R_{2.10\ \mu m}$).

2. A SWIR camera or detectors 14 with spectral filters between about 2.2 and 2.3 μm are used to measure the radiance of the area of interest at about 2.25 μm ($R_{2.25\ \mu m}$).

3. If desirable, the area of interest ahead of a vehicle or an infrastructure is imaged in a visible or another spectral band (e.g., in the visible band).

4. The measurements at 2.10 μm ($R_{2.10\ \mu m}$) and 2.25 μm ($R_{2.25\ \mu m}$) are then used to produce single values or an image of the radiance ratio $\gamma$ (in larger pixels than the original images if gridded filters are used). Areas on which the radiance ratio $\gamma$ is smaller than a pre-established critical value $\gamma_{crit} \approx 0.6$ (a more precise and/or dynamically adjusted value should be determined after calibration of the system) are flagged as containing ice. Since values can be used to determine that ice is likely present (thereby moving to the next steps below), absence of ice detection or where radiance ratio $\gamma$ is larger than the pre-established critical value $\gamma_{crit}$ suggests that no warning should be given.

5. In some embodiments, measurements of reflectance can be used to determine the occurrence of specular reflection. For example, this can be achieved by determining if the reflectance of a single area in the field of view of a detector or of single image pixels is large enough ($R \geq R_{crit}$) to be indicative of specular reflection.

6. In some embodiments, the ground temperature ($T_g$) can be measured by an infrared sensor or estimated based on temperature measurements by a sensor exposed to the airflow. If ice and specular reflection are detected, and $T_g \leq T_{crit} \approx 0°$ C., a visual and/or audible warning indicating the presence of ice conditions can be produced.

Methods of Airborne-Based Applications

Figure 4:
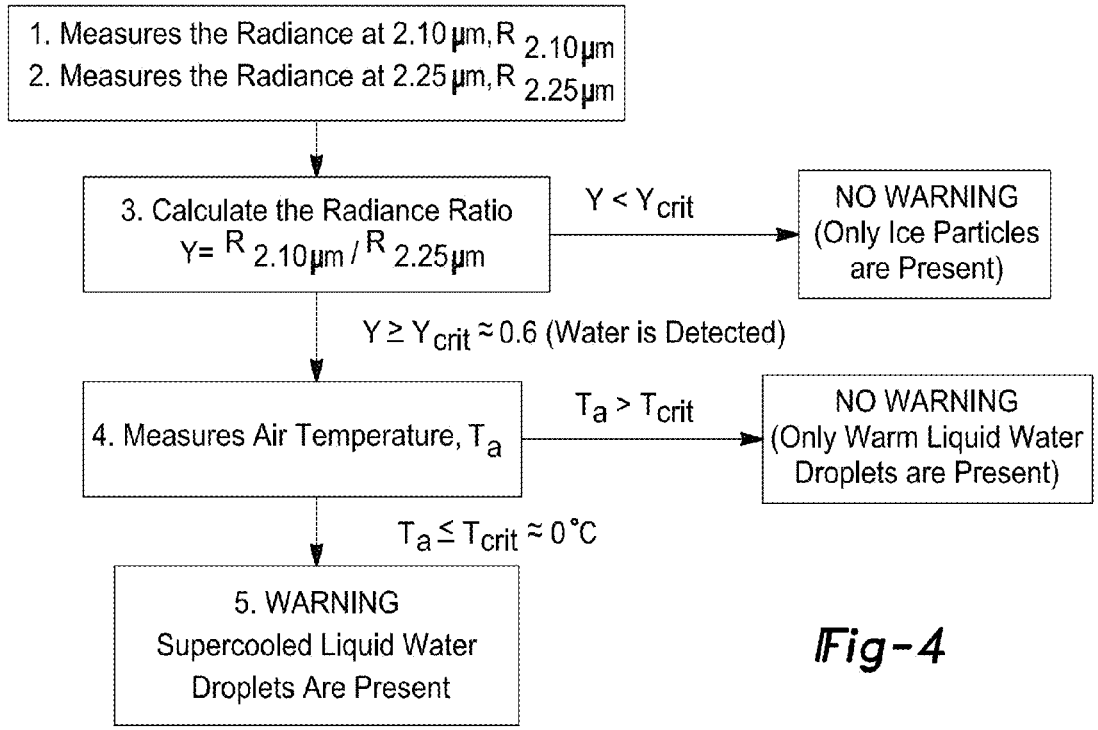
FIG. 4 is a flow chart of an algorithm for determining the presence of supercooled liquid water droplets.
Figure 5A:
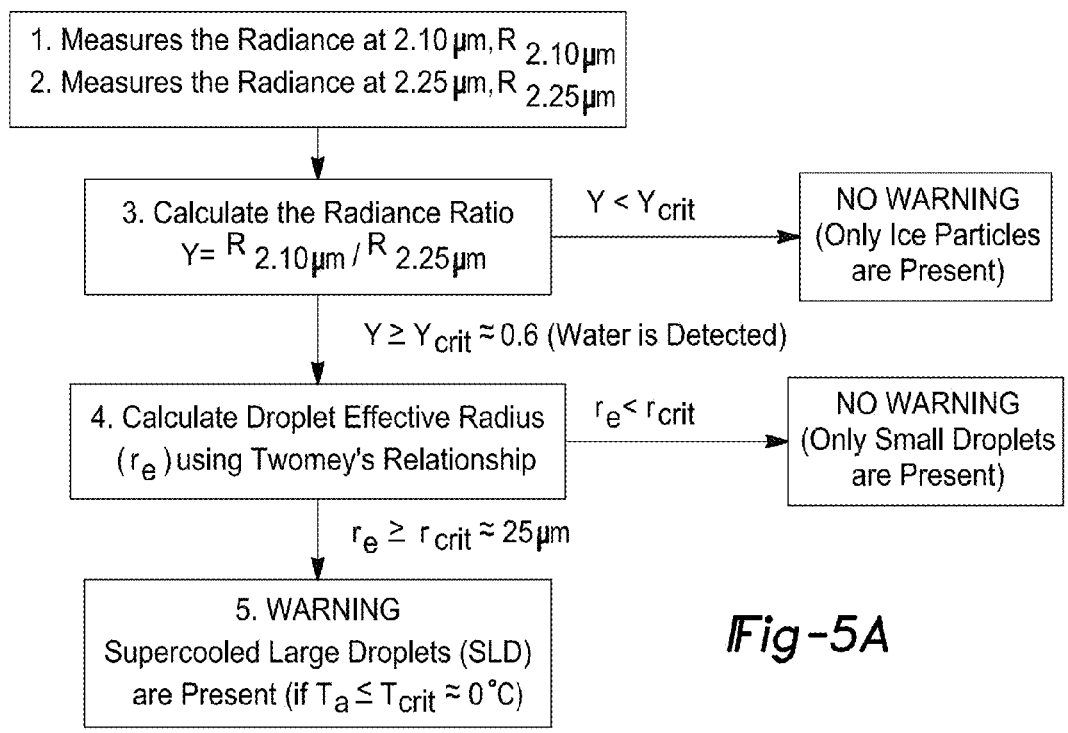
FIG. 5A is a flow chart of an algorithm for determining the presence of Supercooled Large Droplets (SLD) around and/or ahead of vehicles.
Figure 7A:
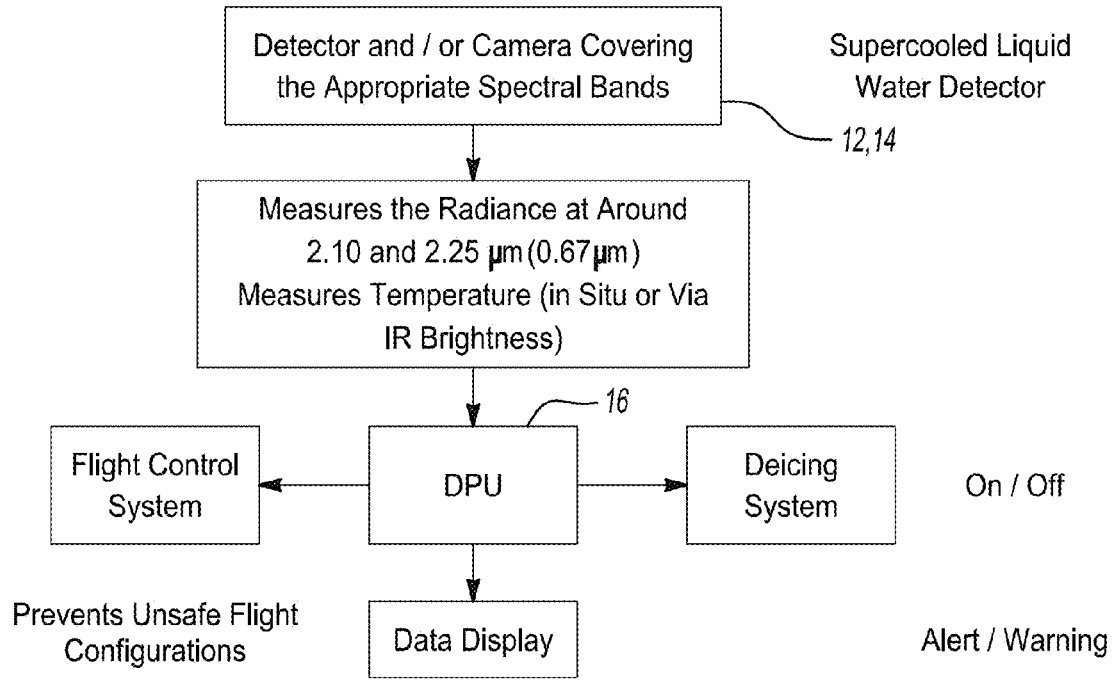
FIG. 7A is a block diagram of the ice and supercooled water detection system according to some embodiments of the present teachings.
Figure 7B:
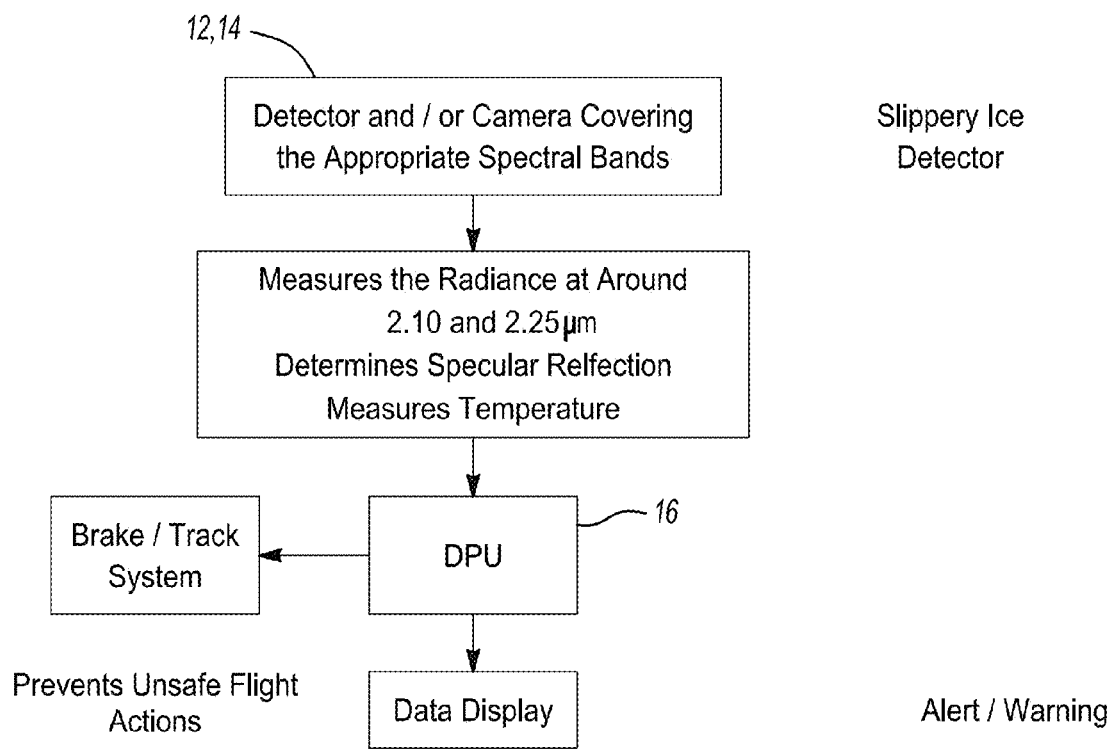
FIG. 7B is a block diagram of the ice and supercooled water detection system according to some embodiments of the present teachings.

According to some embodiments, as illustrated in FIGS. 4, 7B, and 8A, the present teachings provide a system and method for detecting supercooled water droplets that freeze when impacting the surfaces of aircrafts (e.g., airplanes, helicopters, blimps, UAVs) and other objects of interest. The present teachings provide a system for detecting icing hazards in the airspace ahead of aircrafts by detecting the presence of supercooled liquid water droplets in this airspace, and by estimating the size of these droplets. As discussed herein, the present teachings use measurements of radiance in the two spectral bands indicated in FIGS. 1, 2A, 2B, 3A and 3B to estimate the presence of supercooled liquid water droplets in the airspace ahead of aircraft. The present teachings provides a system that alerts a human pilot or an autopilot to icing hazards when liquid water droplets are detected in the airspace immediately ahead of the aircraft and the temperature is below the freezing value.

It should be understood that the methods outlined herein are not limited to the exact order in which they are described because, in many cases, the specific order of operation may be flexible.

In some embodiments, the present system can quantify the hazards level by estimating the size of the supercooled liquid water droplets. The droplet size is estimated based on the radiance in a spectral band around 2.2 μm (or another absorbing spectral band such as around 3.7 μm) and analytical relationships or look up tables such as those constructed based on the relationships depicted in FIGS. 3A and 3B. Measurements of the radiance in a non-absorbing spectral band, for example, around 0.67 μm, can provide a more accurate estimate of the cloud droplet size.

An algorithm for detecting supercooled liquid water is described in FIG. 4. It comprises of the following steps:

1. A SWIR camera or detectors with spectral filters between about 2.05 and 2.15 μm are used to measure the radiance of the area ahead of the aircraft at about 2.10 μm ($R_{2.10\,\mu m}$).

2. A SWIR camera or detectors with spectral filters between about 2.2 and 2.3 μm at are used to measure the radiance of the area ahead of the aircraft at about 2.25 μm ($R_{2.25\,\mu m}$).

3. These two measurements are then used to produce single values or an image of the radiance ratio γ (in larger pixels than the original images if gridded filters are used). Areas on which the radiance ratio γ is larger or equal than a pre-established critical value $\gamma_{crit} \approx 0.6$ (a more precise and/or dynamically adjusted value is determined after calibration of the system) are flagged as containing liquid water droplets.

4. The air temperature (T) at the flight level is measured by a sensor such as a thermocouple exposed to the airflow or any other suitable method. If the temperature is smaller or equal to a pre-established critical value $T_{crit} \approx 0°$ C. the areas flagged as containing liquid water droplets are identified as contained supercooled liquid water droplets. Images of these areas can be colored as desired when displayed (e.g., on the MFD).

5. When the aircraft approaches areas flagged as containing supercooled liquid droplets, the system gives a warning and activates safety systems if desirable.

The present teachings also provide a system for estimating the size of water droplets. The estimation of droplet size is based on radiance measurements and look up tables or analytical relationships constructed based on the relationships depicted in FIGS. 3A and 3B. Algorithms for estimating the cloud droplet size (effective radius) are described in FIGS. 5A and 5B. However, it should be noted that the algorithm of FIG. 5A can be improved by including measurements of radiance at non-absorbing wavelengths (e.g., visible), whereby this measurement can then be used as a reference to correct the radiance values used in the calculation of the droplets' effective radius as set forth in FIG. 5B. The algorithm of FIG. 5A comprises of the steps of:

1. A SWIR camera or detectors with spectral filters between about 2.05 and 2.15 μm are used to measure the radiance of the area ahead of the aircraft at about 2.10 μm ($R_{2.10\,\mu m}$).

2. A SWIR camera or detectors with spectral filters between about 2.2 and 2.3 μm at are used to measure the radiance of the area ahead of the aircraft at about 2.25 μm ($R_{2.25\,\mu m}$).

3. These two measurements are used to produce single values or an image of the radiance ratio γ (in larger pixels than the original images if gridded filters are used). Areas on which the radiance ratio γ is larger or equal than a pre-established critical value $\gamma_{crit} \approx 0.6$ (a more precise and/or dynamically adjusted value should be determined after calibration of the system) are flagged as containing liquid water droplets.

4. The droplets effective radius ($r_e$) is then calculated based on the measurements of radiance at 2.25 μm ($R_{2.25\,\mu m}$) and Twomey's relationship presented in FIG. 3A.

5. The air temperature (T) at the flight level is measured by a thermocouple exposed to the airflow or any other suitable method. Areas on which $T_a \le T_{crit} \approx 0°$ C. and $r_e \ge r_{crit} \approx 25$ μm (or a more precise $r_e$ value determined after calibration of the system) are flagged as likely containing SLD and colored as desired when displayed (e.g., on a Multi Function Display, MFD). Areas with values of $T_a \le T_{crit} \approx 0°$ C. and $r_e >> r_{crit} \approx 25$ μm indicates extremely hazard conditions and can be flagged as such.

Figure 5B:
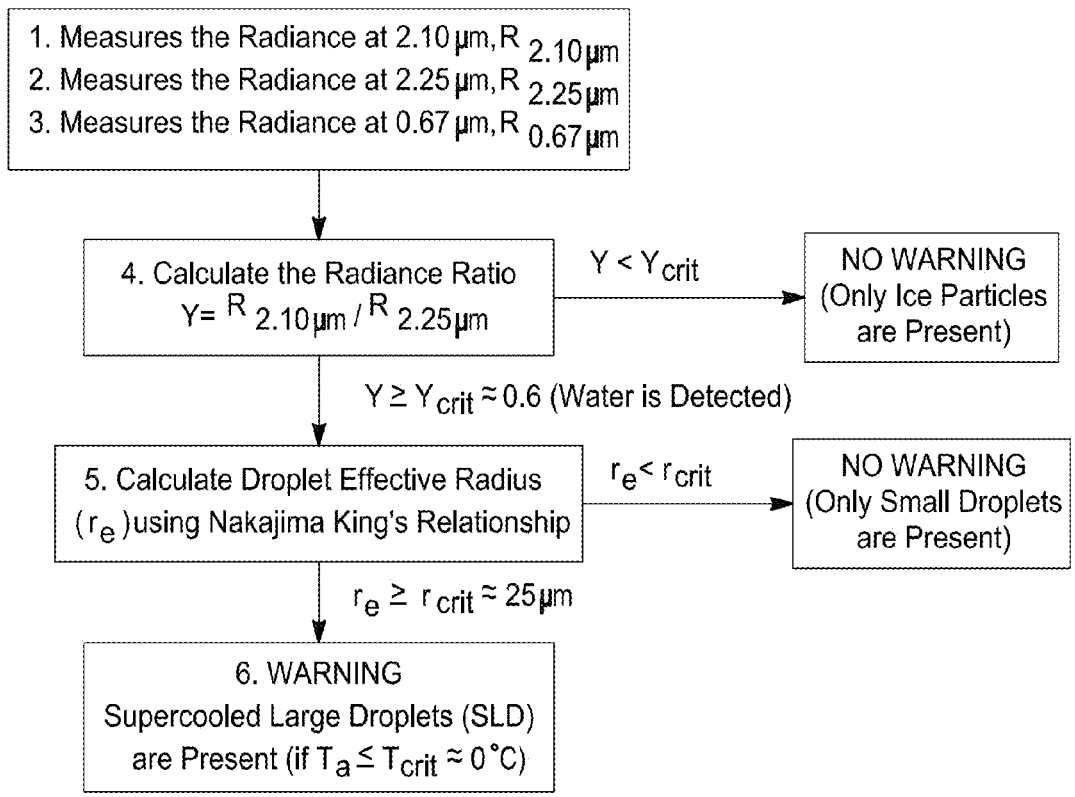
FIG. 5B is a flow chart of an algorithm for determining the presence of SLD when larger accuracy is desirable.

A more sophisticated algorithm for detecting Supercooled Large water Droplets (SLD) is described in FIG. 5B. The algorithm comprises the steps of:

1. A SWIR camera or detectors with spectral filters between about 2.05 and 2.15 μm are used to measure the radiance of the area ahead of the aircraft at about 2.10 μm ($R_{2.10\,\mu m}$).

2. A SWIR camera or detectors with spectral filters between about 2.2 and 2.3 μm at are used to measure the radiance of the area ahead of the aircraft at about 2.25 μm ($R_{2.25\,\mu m}$).

3. A visible (or covering another non-absorbing spectral band) camera or detectors with spectral filters around 0.67 μm (or another non-absorbing band) are used to measure the radiance of the area ahead of the aircraft at about 0.67 μm ($R_{0.67\,\mu m}$).

4. The measurements at 2.10 μm ($R_{2.10\,\mu m}$) and 2.25 μm ($R_{2.25\,\mu m}$) are used to produce single values or an image of the radiance ratio γ (in larger pixels than the original images if gridded filters are used). Areas on which the radiance ratio γ is larger or equal than a pre-established critical value $\gamma_{crit} \approx 0.6$ (a more precise and/or dynamically adjusted value is determined after calibration of the system) are flagged as containing liquid water droplets.

5. The droplets effective radius ($r_e$) is then calculated based on the measurements of radiance at 0.67 μm ($R_{0.67\,\mu m}$) and 2.25 μm ($R_{2.25\,\mu m}$), and Nakajima-King's relationship presented in FIG. 3B.

6. The air temperature (T) at the flight level is measured by a thermocouple exposed to the airflow or any other suitable method. Areas on which $T_a \le T_{crit} \approx 0°$ C. and $r_e \ge r_{crit} \approx 25$ μm (or a more precise $r_e$ value determined after calibration of the system) are flagged as likely containing SLD and colored as desired when displayed (e.g., on a MFD). Areas with values of $T_a \le T_{crit} \approx 0°$ C. and $r_e >> r_{crit} \approx 25$ μm indicates extremely hazard conditions and can be flagged as such. A visual and/or audible WARNING is produced.

In some embodiments, a WARNING can be produced when supercooled liquid water droplets or mixtures of water droplets and ice particles are detected, while an ALERT can be produced when SLD are detected.

It should be understood that although certain features are described in connection with a particular application (e.g. airborne-based applications), this should not be regarded as limiting such certain features to only the particular application, as such certain features may be equally applicable to alternative applications (e.g. ground-based applications on vehicles or infrastructure).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for detecting ice and/or water within an area of interest, said system comprising:

a detection system measuring radiance level of the area of interest when exposed to shortwave infrared (SWIR) radiation having a wavelength in the range of about 2.05 μm to about 2.30 μm, said detection system measuring said radiance level in a first band having a wavelength in the range of about 2.05 μm to about 2.15 μm and outputting a first band signal, said detection system measuring said radiance level in a second band having a wavelength in the range of about 2.15 μm to about 2.30 μm and outputting a second band signal; and a processing unit determining a radiance ratio of said first band signal and said second band signal, said processing unit comparing said radiance ratio to predetermined critical ratio ranges and outputting a determination signal indicating at least one of presence of ice when said radiance ratio is within a first range of said predetermined critical ratio ranges and presence of water when said radiance ratio is within a second range of said predetermined critical ratio ranges.

2. The system according to claim 1, further comprising:
a temperature sensing system determining a temperature of the area of interest and outputting a temperature signal,
wherein said processing unit comparing said temperature signal to a predetermined critical temperature range and outputting said determination signal in response thereto.

3. The system according to claim 1 wherein said processing unit determines existence of specular reflection in the area of interest, said processing unit outputting said determination signal in response to said specular reflection.

4. The system according to claim 1, further comprising:
an auxiliary camera imaging the area of interest and outputting an auxiliary camera output,
wherein said processing unit determines existence of specular reflection in the area of interest based on said auxiliary camera output, said processing unit outputting said determination signal in response to said specular reflection.

5. The system according to claim 1 wherein said processing unit calculates an effective radius of water droplets detected within the area of interest and outputs said determination signal in response thereto.

6. The system according to claim 1, further comprising:
a second detection system measuring radiance in a non-absorbing spectral band in a range of about 0.5 μm to about 0.7 μm and outputting a second detection system signal,
wherein said processing unit uses said second detection system signal, said first band signal, and said second band signal to calculate an effective radius of water droplets detected within the area of interest and outputs said determination signal in response thereto.

7. The system according to claim 1, further comprising:
a second detection system measuring radiance in an absorbing spectral band in a range of about 3.0 μm to about 5.0 μm and outputting a second detection system signal,
wherein said processing unit uses said second detection system signal, said first band signal, and said second band signal to calculate an effective radius of water droplets detected within the area of interest and outputs said determination signal in response thereto.

8. The system according to claim 1 wherein said detection system comprises one or more detectors, each of said one or more detectors being sensitive to said shortwave infrared (SWIR) radiation having said wavelength in the range of about 2.05 μm to about 2.30 μm.

9. The system according to claim 8 wherein said one or more detectors comprises at least two detectors, a first of said at least two detectors being sensitive to a first spectrum range of said about 2.05 μm to about 2.30 μm range and a second of said at least two detectors being sensitive to a second spectrum range of said about 2.05 μm to about 2.30 μm range, said first spectrum range and said second spectrum range being at least partially different.

10. The system according to claim 1 wherein said detection system comprises at least one camera, said at least one camera being sensitive to said shortwave infrared (SWIR) radiation having said wavelength in the range of about 2.05 μm to about 2.30 μm.

11. The system according to claim 10 wherein said detection system further comprises two or more spectral filters operably coupled to said at least one camera, a first of said two or more spectral filters being sensitive to a first spectrum range of said about 2.05 μm to about 2.30 μm range and a second of said at least two detectors being sensitive to a second spectrum range of said about 2.05 μm to about 2.30 μm range, said first spectrum range and said second spectrum range being at least partially different.

12. The system according to claim 1, further comprising:
a data display system displaying an indicia in response to said determination signal.

13. The system according to claim 1, further comprising:
a device or anti-icing system of an airborne-based vehicle being responsive to said determination signal.

14. The system according to claim 1, further comprising:
a flight control system of an airborne-based vehicle being responsive to said determination signal.

15. The system according to claim 1, further comprising:
a brake control system of a ground-based vehicle being responsive to said determination signal.

16. The system according to claim 1, further comprising:
a light source outputting light energy at a wavelength in the range of about 2.05 μm to about 2.30 μm, said light source illuminating the area of interest.

17. The system according to claim 16 wherein said light source is selected from the group consisting of a laser, halogen light, infrared light, and light-emitting diode.

18. A method for detecting ice within an area of interest, said method comprising:
measuring a first radiance level of the area of interest at a first spectral band in the range of about 2.05 μm to about 2.15 μm;
measuring a second radiance level of the area of interest at a second spectral band in the range of about 2.15 μm to about 2.30 μm;
calculating a radiance ratio of said first radiance level and said second radiance level; and
determining whether said radiance ratio is within a predetermined critical radiance ratio range,
if said radiance ratio is within said predetermined critical radiance ratio range then determining if a specular reflection is present by determining if said first radiance is greater than a predetermined critical radiance and outputting an ice-present warning.

19. A method for detecting supercooled liquid water droplets within an area of interest, said method comprising:
measuring a first radiance level of the area of interest at a first spectral band in the range of about 2.05 μm to about 2.15 μm;
measuring a second radiance level of the area of interest at a second spectral band in the range of about 2.15 μm to about 2.30 μm;
calculating a radiance ratio of said first radiance level and said second radiance level; and
determining whether said radiance ratio is within a predetermined critical radiance ratio range,
if said radiance ratio is within said predetermined critical radiance ratio range then measuring a temperature of the area of interest and determining if said temperature is within a predetermined critical temperature range and outputting a supercooled-liquid-water-droplets-present warning.

20. A method for detecting supercooled large droplets (SLD) within an area of interest, said method comprising:
measuring a first radiance level of the area of interest at a first spectral band in the range of about 2.05 μm to about 2.15 μm;
measuring a second radiance level of the area of interest at a second spectral band in the range of about 2.15 μm to about 2.30 μm;
calculating a radiance ratio of said first radiance level and said second radiance level; and
determining whether said radiance ratio is greater than a predetermined critical radiance ratio,
if said radiance ratio is within said predetermined critical radiance ratio then calculating a droplet effective radius and determining if said droplet effective radius is greater than a predetermined critical droplet radius and outputting a supercooled-large-droplets-present warning.

* * * * *